(12) United States Patent
Sojka et al.

(10) Patent No.: US 9,869,678 B2
(45) Date of Patent: Jan. 16, 2018

(54) METHOD FOR DETECTION OF L523S EXPRESSION IN BIOLOGICAL SAMPLES

(71) Applicant: DAKO DENMARK A/S, Minneapolis, MN (US)

(72) Inventors: Katherine Marks Sojka, Oak View, CA (US); Elizabeth Oliver Spaulding, Santa Barbara, CA (US)

(73) Assignee: Dako Denmark A/S, Glostrup (DK)

( * ) Notice: Subject to any disclaimer, the term of this patent is extended or adjusted under 35 U.S.C. 154(b) by 53 days.

(21) Appl. No.: 14/492,171

(22) Filed: Sep. 22, 2014

(65) Prior Publication Data
US 2015/0072891 A1 Mar. 12, 2015

Related U.S. Application Data (63) Continuation of application No. 12/158,223, filed as application No. PCT/DK2006/000732 on Dec. 20, 2006, now abandoned.

(60) Provisional application No. 60/751,833, filed on Dec. 20, 2005, provisional application No. 60/773,212, filed on Feb. 14, 2006.

(51) Int. Cl.
*G01N 33/53* (2006.01)
*G01N 33/574* (2006.01)

(52) U.S. Cl.
CPC ... *G01N 33/57476* (2013.01); *G01N 33/5743* (2013.01)

(58) Field of Classification Search
None
See application file for complete search history.

(56) References Cited

U.S. PATENT DOCUMENTS

| | | | |
|---|---|---|---|
| 4,275,149 A | 6/1981 | Litman et al. | |
| 4,318,980 A | 3/1982 | Boguslaski et al. | |
| 4,737,456 A | 4/1988 | Wang et al. | |
| 5,543,332 A | 8/1996 | Lihme et al. | |
| 6,482,597 B1 | 11/2002 | Wang et al. | |
| 6,518,256 B1 | 2/2003 | Wang et al. | |
| 6,531,315 B1 | 3/2003 | Wang et al. | |
| 6,696,247 B2 | 2/2004 | Wang | |
| 6,830,924 B1* | 12/2004 | Chen | C07K 14/4748 435/252.3 |
| 6,960,750 B2 | 11/2005 | Doane | |
| 6,969,518 B2 | 11/2005 | Hougton et al. | |
| 2002/0052329 A1 | 5/2002 | Wang et al. | |
| 2002/0115139 A1 | 8/2002 | Kalos et al. | |
| 2002/0147143 A1 | 10/2002 | Wang et al. | |
| 2003/0138438 A1 | 7/2003 | Mericle et al. | |
| 2003/0236209 A1 | 12/2003 | Foy et al. | |
| 2005/0142620 A1 | 6/2005 | Bangur et al. | |

FOREIGN PATENT DOCUMENTS

WO    WO 1999/054738 A1    10/1999

OTHER PUBLICATIONS

Caselitz et al, Virchows Arch Pathol Anat, 1983; 400:43-51.*
Jalali et al, Diagn Cytopathol, 2005; 33:78-82.*
Cavazza, A. et al., "Primary Leiomyoma of the Lung, with Clear-Cell Features and Admized Alveolar Spaces: Description of a case presenting with pseumothroax," Pathologica, 95:108-14 (2003).
Cavazza, A. et al., "Solitary Fibrous Pseudopapillary Tumor of the Lung: Pulmonary Fibroadenoma and Adenofibroma Revisited," Pathologica, 95:162-66 (2003).
Davidson, Ben et al., "Malignant Mesothelioma," Ultrastruct Pathol., 28:179-80 (2004).
Extended European Search Report including Search Opinion issued in European Patent Application No. 11075221.9, dated Jan. 18, 2012.
Findeis-Hosey, Jennifer J. et al., "The use of insulin like-growth factor II messenger RNA binding protein-3 in diagnostic pathology," Human Pathology (2011) 42, 303-314, © 2011 Elsevier Inc.
Gill, Capt. Stephen A. et al., "Use of Desmin Immunohistochemistry to Distinguish Between Mesothelial Cells and Carcinoma in Serous Fluid Cell Block Preparations," *Acta Cytologica*, © The International Academy of Cytology, vol. 44, No. 6, Nov.-Dec. 2000, pp. 976-980.
Gress T.M. et al., "A Pancreatic Cancer-Specific Expression Profile," Oncogene, 13:1819-30 (1996).
Istvanic S. et al., "Spectrum of KOC (K Homology Domain Containing Protein Over-Expressed in Cancer) Immunostaining Among Carcinomas of Different Sites," Mod Pathol, 18:298A-299A (Abstract 1381) (2005).
Jiang, Zhong et al., "Analysis of RNA-binding protein IMP3 to predict metastasis and prognosis of renal-cell carcinoma: a retrospective study," http://oncology.thelancet.com, Lancet Oncol., vol. 7, Jul. 2006, pp. 556-564.
Kapanci, Yusuf et al., "Cytoskeletal Features of Alveolar Myofibroblasts and Pericytes in Normal Human and Rat Lung," *The Journal of Histochemistry and Cytochemistry*, vol. 40, No. 12, pp. 1955-1963, © 1992 by the Histochemical Society, Inc.
Köhler, G. et al., "Continuous Cultures of Fused Cells Secreting Antibody of Predefined Specificity," Nature 256:495-7 (1975).
Leong, Anthony S.-Y, et al., "Epitope Retrieval with Microwaves: a comparison of citrate buffer and EDTA with Three Commercial Retrieval Solutions," Appl Immunohistochem, 4:201-07 (1996).
McCluggage, W.G. et al., "An Immunohistochemical Analysis of Ovarian Small Cell Carcinoma of Hypercalcemic Type," Int J Gynecol Pathol., 23:330-36 (2004).

(Continued)

*Primary Examiner* — Mark Halvorson (57) ABSTRACT

The present invention discloses methods for differentiating between normal or reactive cells and malignant cells in biological samples comprising: exposing the biological sample to an antibody to L523S protein and detecting the presence of the antibody bound to L523S protein within the malignant cells, in embodiments, such methods may further comprise: exposing the biological sample to an antibody to a second protein that is a marker of cell lineage and detecting the presence of the antibody to the second protein within cells corresponding to a particular cell lineage and/or may comprise: exposing the biological sample to an antibody to a third protein which is a marker of cells that are normal or reactive and detecting the presence of the antibody to the third protein within cells that are normal or reactive.

15 Claims, 8 Drawing Sheets

(56) References Cited

OTHER PUBLICATIONS

Müeller-Pillasch, Friederike et al., "Cloning of a Gene Highly Overexpressed in Cancer Coding for a Novel KH-Domain Containing Protein," Oncogene, 14:2729-33 (2003).
Nielsen, Jacob et al., "A Family of Insulin-Like Growth Factor II mRNA-Binding Proteins Represses Translation in Late Development," Mol Cel Biol., 19:1262-70 (1999).
O'Sullivan, M.J. et al., "Methods for the Preparation of Enzyme-Antibody Conjugates for Use in Enzyme Immunoassay," Methods in Enzymology, 73:147-66, J. Langone & H. Van Vunakis, eds., Academic Press, New York (1981).
PCT International Search Report for PCT/DK2006/000732 dated Mar. 7, 2007.
Sojka, K.M., et al., "Immunoreactivity of Anti-L523S on Normal and Malignant Lung Pleural Tissue Biopsies," Laboratory Investigation, 86:317A (Abstract 1480) (2006).
Tabatabai, *Lab Invest*, 2003, 83:84A.
Wang, T. et al., "L523S, an RNA-Binding Protein as a Potential Therapeutic Target for Lung Cancer," Br J Cancer, 88:887-94 (2003).
Xu, Haodong et al., "High-Grade Neuroendocrine Carcinomas of the Lung Express K Homology Domain Containing Protein Overexpressed in Cancer but Carcinoid Tumors Do Not," Hum Pathol., 38:555-63 (2007).
Zhao Huiocong et al., "Expression of KOC (L523S) in Pancreatic FNA Cytology for Diagnosing Invasive Pancreatic Adenocarcinoma," Cancer, 108:408 (Abstract 121) (2006).

\* cited by examiner

METHOD FOR DETECTION OF L523S EXPRESSION IN BIOLOGICAL SAMPLES

CROSS REFERENCE TO PRIOR APPLICATIONS

This application is a continuation of U.S. patent application Ser. No. 12/158,223, filed Jun. 19, 2008, which is a national stage filing under 35 U.S.C. §371 of International Application No. PCT/DK2006/000732, filed on Dec. 20, 2006, which claims the benefit of U.S. Provisional Patent Application No. 60/751,833, filed on Dec. 20, 2005, and U.S. Provisional Patent Application No. 60/773,212, filed on Feb. 14, 2006, all of which are incorporated herein by reference.

TECHNICAL FIELD

The present invention relates to the use of an antibody to L523S in the differentiation of malignant cells from benign, reactive or normal cells in biological samples.

BACKGROUND OF INVENTION

Some of the primary challenges faced by pathologists in cancer diagnoses relate to distinguishing between different types of malignancies and differentiating between benign and malignant cell proliferations.

One example of such type of challenge is in the diagnosis of lung neuroendocrine tumors, the spectrum of which includes typical carcinoid, atypical carcinoid, large cell neuroendocrine carcinoma (LCNEC) and small cell carcinoma (SCLC). This spectrum of lung neuroendocrine tumors provides a range of phenotypically distinct entities with different biological behaviors. Although various types of lung neuroendocrine tumors share common neuroendocrine features, they differ greatly in their cytogenetic and molecular characteristics, highlighting a fundamental molecular divergence among these tumors. Importantly, they exhibit different degrees of aggressiveness, with typical carcinoid and SCLC representing the two extremes of malignancy.

In the second instance, benign conditions, including inflammatory conditions, infectious processes and benign cell proliferations can be difficult to distinguish from malignancy. As one example, the positive identification of malignant cells in lung pleural tissue biopsies and in pleural effusions can be challenging, particularly when both normal and reactive mesothelial cells are present. Pathologists generally rely on characteristic histologic features to aid in differentiating between benign and malignant conditions, however benign/reactive cells can often share these histologic features with malignant cells. Furthermore, when evaluating specimens derived from biologic fluids and needle biopsies, it can be difficult to obtain specimens with sufficient morphologic detail for clinical diagnosis. Another example is in differentiating benign melanocyte nevi from malignant melanoma. Benign nevi, especially in those with atypical features can be difficult to distinguish from malignant melanoma.

Another approach, which has lately been widely used in cancer diagnostics, is molecular diagnostics. There have been described numerous molecular markers of cancer cells, such as particular abnormalities in genetic material associated with particular forms of cancer, abnormalities on the transcription level, specific profiles of the expressed proteins.

L523S protein is one of the promising molecular markers of cancer cells which can be used for the molecular cancer diagnostics. The protein is also known as K homology domain containing protein overexpressed in cancer (KOC), which has been described by Muelter-Pillasch et al. (Oncogene 1997, 14(22), pp. 2729-2733) and by Nielsen et al. (Mol. Cell Biol. 1999, 19(2), pp. 1262-1270). Nielsen et al. (Mol. Cell Biol. 1999, 19(2), pp. 1262-1270) have determined that L523S (KOC) is identical to IMP3, a member of the insulin-like growth factor II (IGF-II) mRNA-binding protein (IMP) family. The L523S protein is a 580 amino acid oncofetal RNA binding protein that has four K homology domains and that regulates insulin-like growth factor II (IGF-II) transcripts during embryogenesis. L523S is later re-expressed in a proportion of cancer cells from various types of tumors, including pancreatic and lung adenocarcinoma, and it may function in promoting tumor cell proliferation by enhancing IGF-II protein expression.

Evidence has previously been presented (for instance, in US Patent Application Publications 2003/0236209 A1, 2003/0138438 A1 and 2002/0147143 A1) indicating that L523S may also be present in colon adenocarcinomas, prostate adenocarcinomas, CML, AML, Burkitt's Lymphoma, brain tumors, retinoblastomas, ovarian tumors, teratocarcinomas, uterus myosarcomas, germ cell tumors as well as pancreatic and cervical tumor cell lines. Since it was first identified in pancreatic carcinomas by Gress, et al. (Oncogene 1996, 13, pp. 1819-1830), the marker L523S has been detected in non-small cell carcinomas of the lung as well as other human malignancies. In particular, immunohistochemical studies have indicated L523S expression is a marker of increasingly aggressive biologic potential among pancreatic ductal lesions (Istvanic et al., Mod. Pathol. 2005, 18(S1); pp. 298A-299A). Strong and diffuse immunohistochemical expression of this marker is highly sensitive for the identification of invasive carcinoma and can be found in both severely dysplastic lesions as well as carcinomas of the pancreas. In addition, Jiang et al. (Lancet Oncol. 2006, 7, pp. 556-564) have shown that L523S is expressed in renal cell carcinoma.

Various DNA encoding sequences for and amino acid sequences of L523S have been taught in U.S. Pat. Nos. 6,969,518; 6,960,570; 6,696,247; 6,531,315; 6,518,256; 6,482,597 and in United States Patent Application Publications 2003/0236209 A1; 2003/0138438 A1; 2002/0147143 A1; 2002/0115139 A1 and 2002/0052329 A1.

Using rtPCR and microarray analyses, it has been found (Wang et al., Br J Cancer 2003, 88(6), pp. 887-894) that L523S mRNA expression is minimal in many normal tissues. Importantly, however, L523S is widely expressed in many malignancies. Istvanic et al. (Mod. Pathol. 2005, 18(S1); pp. 298A-299A) have found that a subset of carcinomas from various organs—lung, pancreas, esophagus, stomach, colorectum, cervix and bladder—express the L523S protein. The restricted and relatively low level expression of L523S in a subset of normal tissue types compared to its presence in many different forms of cancer make it a potential marker of malignancy.

Despite of accumulated evidence indicating that expression of the L523S protein is associated with metastatic potential of cancer cells, full diagnostic and prognostic potential of estimating the expression of L523S protein in cells for molecular diagnostics of cancer and, thus, the value of L523S protein a cancer biomarker have not been investigated.

SUMMARY OF INVENTION

The present invention relates to use of L523S protein as a cancer biomarker in methods for diagnosis, prognosis, monitoring of cancer and treatment decisions, which based on immunodetection of the protein in malignant cells of biological samples and, thus, differentiating between normal or reactive cells and malignant cells of said biological samples. According to the invention differentiating between cells of the samples is possible because the expression of L523S can be detected only in malignant cells but not in normal or reactive cells present in the samples.

In general, a cancer may be detected in a patient by immunohistochemical test methods or flow cytometry based on the presence of one or more distinctive tumor proteins in a biological sample (for example, blood, sera, sputum, pleural fluid, peritoneal fluid, urine and/or tumor tissue biopsies) obtained from the patient. In other words, such proteins may be used as markers to indicate the presence or absence of a cancer such as lung cancer. In addition, such proteins may be useful for the detection of other cancers.

There are a variety of assay formats known to those of ordinary skill in the art for using a binding agent to detect polypeptide markers in a sample. In general, one commonly used detection assay format will comprise the steps of (a) contacting a biological sample obtained from a patient with a binding agent such as an antibody or antibodies; (b) detecting in the sample a level of polypeptide that binds to the binding agent, possibly by detecting a label associated with the antibody or antibodies. The level of polypeptide bound to the binding agent is commonly concerned with the presence or absence of a disease.

The present invention employs anti-L523S antibodies to distinguish between benign and malignant cells in various biological samples. Such biological sample could be from either humans or animals and could be histological samples, e.g. tissue and/or cell specimens, including cell lines, tissues, cell preparations, blood, bodily fluids, other biological fluids, bone marrow, cytology specimens, blood smears, thin-layer preparations, imprints, cytospins, cell block sections, micro-arrays, and, frequently, biological samples, such as biopsy specimens, disposed on microscope slides.

In addition, the invention uses an antibody to a marker of cell lineage together with anti-L523S to aid in the clinical evaluation by determining the tissue of origin of cells, which can be important for prognosis and for treatment decisions. Furthermore, the invention employs antibodies to proteins whose expression is restricted to benign/reactive cells in the panel to confirm the diagnosis of benign processes.

Thus, a first aspect the invention relates to a method for differentiating between normal or reactive cells and malignant cells in biological samples characterized by:
   exposing the biological sample to an antibody to L523S protein; and
   detecting the presence of the antibody bound to L523S protein within the malignant cells.

Another aspect of the invention relates to a method for differentiating between normal or reactive cells and malignant cells in a tissue sample characterized by:
   exposing a first portion of the tissue sample to an antibody to L523S protein; and
   detecting the presence of the antibody bound to L523S protein within the malignant cells.

Still, in another aspect, the invention relates to a method for differentiating between normal or reactive cells and malignant cells in a biological sample comprising a cell monolayer or cell pellet derived from a biological fluid characterized by:
   exposing a first portion of the biological sample to an antibody to L523S protein; and
   detecting the presence of the antibody bound to L523S protein within the malignant cells.

All abovementioned aspects of the invention may comprise detection of other biomarkers specific for reactive and/or normal cells which may be present in a sample selected for the immunochemical detection of the L523S protein. As mentioned above, such detection may be advantageous to the diagnosis of benign processes or treatment decisions. In embodiments which comprise such detection, the abovementioned methods may comprise exposing the biological sample to an antibody to a second protein that is a marker of cell lineage and detecting the presence of the antibody to the second protein within cells corresponding to a particular cell lineage. In embodiments, such methods may further comprise exposing the biological sample to an antibody to a third protein which is a marker of cells that are normal or reactive and detecting the presence of the antibody to the third protein within cells that are normal or reactive. The second protein may be calretinin and the third protein may be desmin. The detecting steps may comprise immunohistochemical staining or flow cytometry.

Still, a further aspect of the invention relates to a panel of biomarkers which may be used for the purpose of differentiating between normal or reactive cells and malignant cells in a biological sample. Further, the invention relates to a kit for the differentiation between normal or reactive cells and malignant cells in a biological sample, wherein the kit comprises a panel of antibodies to the proteins of the described panel, wherein at least one of the antibodies is an anti-L523S antibody, at least one another antibody is an antibody a second protein which a marker of a particular cell lineage, and at least one another antibody is an antibody to a third protein which is a marker of cells that are normal or reactive. In particular such kit comprises an anti-L523S antibody, an antibody to calretinin and antibody to desmin.

DISCLOSURE OF INVENTION

In order to overcome the aforementioned challenges in the art, novel methods for detection of L523S expression in biological samples are herein disclosed.

Before the present invention is described, it is to be understood that this invention is not limited to the particular embodiments described, as such methods, devices, and formulations may, of course, vary. It is also to be understood that the terminology used herein is for the purpose of describing particular embodiments only, and is not intended to limit the scope of the present invention which will be limited only by the appended claims. It must be noted that as used herein and in the appended claims, the singular forms "a," "an," and "the" include plural referents unless the context clearly dictates otherwise, and includes reference to equivalent steps and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the specific methods and/or materials in connection with which the publications are cited.

1. Methods for Differentiating Between Normal or Reactive Cells and Malignant Cells As it is mentioned above a first aspect of the invention relates to a method for differentiating between normal or reactive cells and malignant cells in biological samples characterized by:

exposing the biological sample to an antibody to L523S protein; and detecting the presence of the antibody bound to L523S protein within the malignant cells.

By the term "differentiating" in the present context is meant to identify a difference between cells present in a biological sample, in particular in a sample which comprise a plurality of cells corresponding to different cell lineages, such as for example cells of a biopsy sample. By "cell lineage" is meant a pedigree of cells related through mitotic division. Some embodiments of the invention particularly relate, but not limited, to mesothelial cell lineages, which may be morphologically characterized by the presence of flattened epithelial cells of mesenchymal origin that line the serous cavities of the body.

By "biological sample" is meant a sample comprising biological material, in particular a sample of comprising cells, e.g. a sample comprising cells derived from a cell culture, for example cell pellet or cell suspension, sample of body tissue or body fluid, biopsy sample. By "tissue sample" is meant a collection of similar cells obtained from a tissue of a subject or patient, preferably containing nucleated cells with chromosomal material. The four main human tissues are (1) epithelium; (2) the connective tissues, including blood vessels, bone and cartilage; (3) muscle tissue; and (4) nerve tissue. The source of the tissue sample may be solid tissue as from a fresh, frozen and/or preserved organ or tissue sample or biopsy or aspirate; blood or any blood constituents; bodily fluids such as cerebral spinal fluid, amniotic fluid, lung pleural effusion, peritoneal fluid, or interstitial fluid; cells from any time in gestation or development of the subject. The tissue sample of the invention may also be primary or cultured cells or cell lines. The tissue sample may contain compounds which are not naturally intermixed with the tissue in nature such as preservatives, anticoagulants, buffers, fixatives, nutrients, antibiotics, or the like.

In one embodiment of the invention, the biological sample is a biopsy sample, in another embodiment of the invention the biological sample is a sample of any tissue identified above, in another embodiment the biological sample may be a sample of bodily fluids, in still another embodiment the biological sample may be a sample of cell specimens, including cell lines, tissues, cell preparations, blood, other biological fluids, bone marrow, cytology specimens, blood smears, thin-layer preparations, imprints, cytospins, cell block sections, micro-arrays, and, frequently, biological samples, such as biopsy specimens, disposed on microscope slidescultured cells or a sample derived from cultured cells, such as cell pellet or culture medium collected from cultured cells. Particular non-limited examples of the invention include a biopsy of pigmented skin lesion, monolayer or pellet or cell block section derived from a biological fluid, wherein the fluid is lung pleural effusion.

The above mentioned and below described methods include according to the invention assaying biological samples for the presence of particular cells, such as malignant, normal and/or reactive cells by employing antibodies to specific biomarkers of said cells.

The term "antibody" refers to an immunoglobulin molecule or a fragment thereof having the ability to specifically bind to a particular antigen. The antibody may be an anti-marker protein antibody specific for the protein used in the assay. Thus, the antibody may be capable of specifically binding the protein marker as the antigen. Antibodies and methods for their manufacture are well known in the art of immunology. The antibody may be produced, for example, by hybridoma cell lines, in which case the antibody will be capable of specific binding to a single specific site on the antigen termed "epitope", and the antibody characterized by this feature is termed "monoclonal antibody", by immunization to elicit a polyclonal antibody response, which means that an antibody capable of recognizing multiple sites, epitopes, on the antigen is produced, or by recombinant host cells that have been transformed with a recombinant DNA expression vector that encodes the antibody. Antibodies include but are not limited to immunoglobulin molecules of any isotype (IgA, IgG, IgE, IgD, IgM), and active fragments including Fab, Fab', F(ab')$_2$, Facb, Fv, ScFv, Fd, V$_H$ and V$_L$.

Examples of antibodies include but are not limited to single chain antibodies, chimeric antibodies, mutants, fusion proteins, humanized antibodies and any other modified configuration of an immunoglobulin molecule that comprises an antigen recognition site of the required specificity. The invention relates to any type of antibody molecule or a fragment thereof which is suitable for use in the methods disclosed herein. The invention relates to antibody fragments which remain the capability of the corresponding antibody to specifically bind to the antigen. The invention relates to both primary and secondary antibodies. The "primary antibody" is an antibody which is specific for a particular antigen. By "secondary antibody" is meant an antibody which is capable of specifically recognizing an immunoglobulin molecule. Thus, the secondary antibody may be defined as an antibody against the primary antibody.

As it has already been mentioned an antibody of the invention may be any antibody or a fragment thereof, however, in some embodiments, a monoclonal antibody may be preferred. Monoclonal antibodies contain only one single species of antibody combining site, or paratope, capable of immunoreacting with a particular epitope. However, a monoclonal antibody may comprise more than one specific antibody combining site, such antibodies being polyspecific, e.g. bispecific. Suitably the present monoclonal antibodies are monospecific and comprise a single paratope specific for the marker to be detected.

The preparation of antibodies including antibody fragments and other modified forms is described, for example, in "Immunochemistry in Practice," Johnstone and Thorpe, Eds., Blackwell Science, Cambridge, Mass., 1996; "Antibody Engineering," $2^{nd}$ edition, C. Borrebaeck, Ed., Oxford University Press, New York, 1995; "Immunoassay", E. P. Diamandis and T. K. Christopoulos, Eds., Academic Press, Inc., San Diego, 1996; "Handbook of Experimental Immunology," Herzenberg et al., Eds, Blackwell Science, Cambridge, Mass., 1996; and "Current Protocols in Molecular Biology" F. M. Ausubel et al., Eds., Greene Pub. Associates and Wiley Interscience, 1987, the disclosures of which are incorporated herein. In particular, the preparation of monoclonal antibodies, which is well known in the art, was first disclosed by Koehler and Milstein, Nature, 256: 495-497, 1975.

Assaying the samples include a step of detecting the antibody bound to the corresponding biomarker. Accordingly, an antibody of the invention may be detectably labeled. Numerous labels are available which can be generally grouped into the following-categories:
 (a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Coligen et al., Ed. Wiley-lnterscience, New York, N.Y., Pubs. (1991) for example and radioactivity can be measured using scintillation counting.
 (b) Colloidal gold particles.
 (c) Fluorescent labels including, but are not limited to, rare earth chelates (europium chelates), Texas Red, rhodamine, fluorescein, dansyl, Lissamine, umbelliferone, phycocrytherin, phycocyanin, or commercially available fluorophores such SPECTRUM ORANGE® and SPECTRUM GREEN® and/or derivatives of any one or more of the above. The fluorescent labels can be conjugated to the antibody using the techniques disclosed in Current Protocols in Immunology, supra, for example. Fluorescence can be quantified using a fluorimeter.
 (d) Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uncase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147-166 (1981).

Examples of enzyme-substrate combinations include, for example:
 (i) Horseradish peroxidase (HRP) with hydrogen peroxidase as a substrate, wherein the hydrogen peroxidase oxidizes a dye precursor [e.g., orthophenylene diamine (OPD) or 3,3',5,5'-tetramethyl benzidine hydrochloride (TMB)];
 (ii) alkaline phosphatase (AP) with para-Nitrophenyl phosphate as chromogenic substrate; and
 (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Numerous other enzyme-substrate combinations are available to those skilled in the art. For a general review of these, see U.S. Pat. Nos. 4,275,149 and 4,318,980.

Sometimes, the label may be indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody may be conjugated with a small hapten and one of the different types of labels mentioned above is conjugated with an anti-hapten antibody. Thus, indirect conjugation of the label with the antibody can be achieved. In some embodiments of the invention one or more secondary antibody molecules may be conjugated with a label-conjugated polymer backbone. Thus, amplification of the signal may be achieved.

Indirectly and directly labeled secondary antibodies are also commercially available. For example, one example of commercially available label-conjugated polymer backbone carrying secondary antibody molecules reagent is EnVision™ reagent (DAKO). A secondary antibody carrying a label aimed for a particular type of detection may be obtained from numerous manufacturers.

According to the invention, detecting the antibody bound to a marker protein, such as L523S or other protein of the invention, may comprise detecting an immunohistochemical stain. Thus, a method for differentiating between normal or reactive cells and malignant cells in biological samples comprising a step of immunohistochemical detection (IHC) of a marker protein is one of the embodiments of the invention.

Two general methods of IHC are available at present: direct and indirect assays. According to the first assay, binding of antibody to the target protein is determined directly. This direct assay uses a labeled reagent, such as a fluorescent tag or an enzyme-labeled primary antibody, which can be visualized without further antibody interaction. Such detection is preferred embodiment of the invention. In a typical indirect assay, unconjugated primary antibody binds to the protein-antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody. Using labeled secondary antibodies is another preferred embodiment of the invention. Further amplification of the signal maybe achieved when a detection method comprises using a label-conjugated polymer backbone that carries a number of secondary antibody molecules. Such method is another embodiment of the invention. Particular embodiments of these detection methods relate to an enzyme-labeled secondary antibodies and enzyme-conjugated polymer backbone that carries secondary antibody molecules. The examples of enzymes may be selected but not limited to commonly used horse radish Peroxidase (HRP) or alkaline phosphatase (AP).

The sample preparation procedures, treatment of the tissue section prior to, during or following IHC may be desired, For example, epitope retrieval methods, such as heating the tissue sample in citrate buffer may be carried out [see, e.g., Leong et al. Appl. Immunohistochem. 4(3):201 (1996)].

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation.

A signal for the bound antibody may be amplified by using well-known in the art methods and reagents available from commercial manufacturers.

Specimens thus prepared may be mounted and cover-slipped. Slide evaluation is then determined, e.g. using a microscope.

The extent of binding of antibody to the sample is determined by using any one of the detectable labels discussed above. Some times may be preferred the label which is an enzymatic label (e.g. horse radish peroxidase) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

The antibodies and labeled antibodies according to the invention may be used in a variety of immunoimaging or immunoassay procedures to detect the presence of cells expressing the L523S protein or cells expressing other marker protein in a biological sample. This aims to detect a cancer in a patient or monitor the status of such cancer in a patient already diagnosed to have it. When used to monitor the status of a cancer a quantitative immunoassay procedure may be used. Such monitoring assays are carried out periodically and the results compared to determine whether the patient's tumor burden has increased or decreased. Common assay techniques that may be used include direct and indirect assays. Direct assays involve incubating a tissue sample or cells from the patient with a labeled antibody. If the sample comprise L523S protein bearing cells such as includes lung cancer or cells chosen from the group consisting of melanoma, mesothelioma, lung adenocarcinoma, spindle cell carcinoma, squamous cell carcinoma, colonic adenocarcinoma, ovarian carcinoma, gastric carcinoma, pancreatic carcinoma, astrocytoma, Hodgkin's lymphoma, lymphoma, malignant fibrous histocytoma, Ewing's sarcoma and carcinoid, the labeled antibody of the invention will bind to those cells. After washing the tissue or cells to remove unbound labeled antibody, the tissue sample is read for the presence of labeled immune complexes.

Labeled by antibodies cells in fluid samples may be identified by flow cytometry which is commonly used for this purpose in the art.

All the above disclosed embodiments relate to all methods of the invention aimed for the differentiating between normal or reactive cells and malignant cells in biological samples. In particular, these methods include methods comprising detecting a single biomarker of malignant cells, the L523S protein, such as:

1. a method for differentiating between normal or reactive cells and malignant cells in biological samples characterized by:
    exposing the biological sample to an antibody to L523S protein; and
    detecting the presence of the antibody bound to L523S protein within the malignant cells;

2. a method for differentiating between normal or reactive cells and malignant cells in a tissue sample characterized by:
    exposing a first portion of the tissue sample to an antibody to L523S protein; and
    detecting the presence of the antibody bound to L523S protein within the malignant cells.

3. a method for differentiating between normal or reactive cells and malignant cells in a biological sample comprising a cell monolayer, pellet or cell block section derived from a biological fluid characterized by:
    exposing a first portion of the biological sample to an antibody to L523S protein; and
    detecting the presence of the antibody bound to L523S protein within the malignant cells;

In some embodiments the methods of the inventions may include one or more additional steps comprising detecting the presence of one or more other protein markers specific for other particular types of cells present in the analyzed samples. In particular, the invention relates to methods for differentiating between normal or reactive cells and malignant cells in biological samples which comprise the steps of exposing the biological sample or a portion thereof to an antibody to L523S protein and detecting the presence of the antibody bound to L523S protein within the malignant cells, and one or more additional steps, such as the steps of:
    exposing the biological sample, or a portion thereof, to an antibody to a second protein that is a marker of cell lineage;

and detecting the presence of the antibody to the second protein within cells corresponding to a particular cell lineage; and/or the steps of exposing the biological sample, or a portion thereof, to an antibody to a third protein which is a marker of cells that are normal or reactive; and detecting the presence of the antibody to the third protein within cells that are normal or reactive.

In particular, the invention relates to one or more other protein markers selected from protein markers of normal or reactive, or proteins that are markers of particular cell lineages. Specifically, the invention relates to calretinin as a marker of a particular cell lineage, e.g. a mesothelial cell lineage, and desmin as a marker of normal or reactive cells, such as benign cells. However, the invention is not limited to these particular protein markers. A selection of such protein marker will in most embodiments depend on particular type of biological sample to be analyzed, depending on cellular phenotypes present in the sample.

By "portion" of biological sample, in particular "portion" of tissue sample is meant a "section" or "part" of a solid or fluid sample or cell sample by which is meant a single part or piece of said sample, e.g. a thin slice of tissue or cells cut from a tissue sample. It is understood that multiple sections of tissue samples may be taken and subjected to analysis according to the present invention, provided that it is understood that the present invention comprises a method whereby the same section of biological sample may be analyzed at both morphological and molecular levels, or is analyzed with respect to one or more molecular markers, e.g. L523S, desmin and/or calretinin. In some embodiments different portions of the same solid tissue sample or biological fluid sample may be analyzed for the presence of different molecular markers described herein.

All methods of the invention may comprise one or more further sub-steps, such as detection sub-steps steps which may improve or enhance the signal, for example the sub-steps of:

further exposing the biological sample, or a portion thereof, to a labeled secondary antibody that reacts with the antibody bound to L523S protein, or with the antibody bound to a protein which is a marker of cells that are normal or reactive, or with the antibody bound to a protein which is a marker a particular cell lineage; and detecting the presence of the labeled secondary antibody; or sub-steps of:

further exposing the biological sample, or a portion thereof, to a labeled reagent comprising an enzyme-conjugated polymer backbone that carries secondary antibody molecules that react with the antibody bound to L523S protein, or with the antibody bound to a protein which is a marker of cells that are normal or reactive, or with the antibody bound to a protein which is a marker a particular cell lineage; and detecting the presence of the labeled reagent.

According to the invention the above described methods are useful for differentiating between normal or reactive cells and malignant cells in biological samples wherein the type of malignant cells is chosen from the group consisting of melanoma, mesothelioma, lung adenocarcinoma, spindle cell carcinoma, squamous cell carcinoma, colonic adenocarcinoma, ovarian carcinoma, gastric carcinoma, pancreatic carcinoma, asctrocytoma, Hodgkin's lymphoma, lymphoma, malignant fibrous histocytoma, Ewing's sarcoma and carcinoid 2. Protein Panels and Kits The present invention also discloses a panel of protein markers which are useful for differentiating between normal or reactive cells and malignant cells in biological samples, said panel comprising a marker of malignant cells, a marker of normal or reactive cells and a marker of cells of a particular cell lineage. Particularly, the invention relates to a panel consisting of L523S protein as a marker of malignant cells, desmin as a marker or normal or reactive cells, and calretinin as a marker of a particular cell lineage. Use of this panel of protein markers can be aid in the clinical evaluation by determining the tissue of origin of cells, which can be important for prognosis and for treatment decisions. The markers are identified in the corresponding cells by antibodies to these markers. Accordingly, in a further aspect, the invention relates to a kit which comprises a panel of antibodies capable of recognizing the panel of biomarkers identified above. The panel of antibodies according to the invention comprises at least one antibody reagent to a protein marker of malignant cells, at least antibody reagent to a protein marker of a particular cell lineage and/or at least one antibody reagent to a protein marker of normal or reactive cells. In some embodiments the panel may comprise two or more different antibody reagent to any of the members of the abovementioned panel of biomarkers, wherein at least one of said antibodies is capable of recognizing and specifically binding to a marker of malignant cells and at least one another antibody is capable of recognizing and specifically binding to a marker of a particular cell lineage. Preferably, the malignant cell marker is L523S protein, the normal or reactive cell marker is desmin, and the cell lineage marker is calretinin.

A kit comprising a panel of antibodies of the invention may comprise both primary antibodies and secondary antibodies. In such embodiment the secondary antibodies may contain a detectable label. In some embodiments the kit may contains several different secondary antibodies which may comprise different labels. This may be aid to simultaneous detection of the panel biomarker described above. In some embodiments the kit may comprise only primary antibodies. In some embodiments the primary antibodies of such kit may be labeled. Preferably, the primary antibodies comprised by the kit are monoclonal antibodies.

The may also comprise other reagents necessary for the detection of the label.

A particular kit of the invention may consists of an antibody to L523S protein, an antibody to desmin and an antibody to a marker of a particular cell lineage and further comprises one or more non-primary antibody reagents. Another particular kit may consists of an antibody to L523S protein, an antibody to calretinin and an antibody to a marker of cells with are normal or reactive, and further comprises one or more non-primary antibody reagents. In still another particular embodiment the kit may comprise an antibody to L523S protein, an antibody to desmin and an antibody to calretinin, and further comprises one or more non-primary antibody reagents. The wording "comprise" in the present context means that the kit consists of the indicated antibodies and other reagents, which are not primary antibodies to other protein markers. However, in some embodiments, the kits of the invention may further comprise additional primary antibody reagents to other cell markers of the discussed above cellular types, i.e. malignant cell markers, normal or reactive cell markers and cell lineage markers A kit comprising the panel of antibodies to the markers described above is successfully used for analysis of cells of biopsy samples of pigmented skin and diagnosis of melanoma. Therefore, a kit comprising such panel of antibodies may be in one embodiment aimed for the detection of melanoma. In other embodiments the kit may be used for the detection of mesothelioma, lung adenocarcinoma, spindle cell carcinoma, squamous cell carcinoma, colonic adenocarcinoma, ovarian carcinoma, gastric carcinoma, pancreatic carcinoma, astrocytoma, Hodgkin's lymphoma, lymphoma, malignant fibrous histocytoma, Ewing's sarcoma or carcinoid

EXAMPLES

MATERIALS: In a first set of experiments, formalin-fixed paraffin embedded (FFPE) human lung pleural tissue biopsies were obtained and immunohistochemically examined. These samples were derived from twenty-eight cases consisting of nine normal lung pleura and lung pleura containing the following malignancies: mesothelioma (thirteen cases), melanoma (a single case), adenocarcinoma (three cases), spindle cell carcinoma (a single case) and squamous cell carcinoma (a single case). Two cases of normal pericardial tissue containing an intact mesothelial layer were also obtained. Additionally, FFPE biopsies of malignant tumors of colonic adenocarcinoma, ovarian carcinoma, gastric carcinoma, pancreatic carcinoma, astrocytoma, Hodgkin's lymphoma, lymphoma, malignant fibrous histocytoma, Ewing's sarcoma and carcinoid were obtained and examined. Some of the tissue samples were provided by the Cooperative Human Tissue Network, which is funded by the National Cancer Institute.

In another set of experiments, a total of forty-six surgically resected lung neuroendocrine tumor specimens from forty-six patients were immunohistochemically studied according to the methods of the invention. These samples were retrieved from the surgical pathology archives from January 1996 to March 2006 at University of Rochester Medical Center and from January 1994 to January 2005 at Washington University Medical Center. These lung neuroendocrine tumor specimens included sixteen typical carcinoids, six atypical carcinoids, fourteen LCENCs and ten SCLCs.

In a third set of experiments, fifty-one samples with paraffin embedded pleural effusion cell blocks were retrieved and immunohistochemically studied according to methods of the invention. These samples had previously been diagnosed as either benign (sixteen) or malignant pleural effusion (thirty-five, including ten malignant mesotheliomas, ten lung adenocarcinomas, seven breast adenocarcinomas, four colonic adenocarcinomas, three small cell carcinomas and a single squamous cell carcinoma).

In a fourth set of experiments, eighty slides containing benign urothelium and various urothelial lesions were immunohistochemically studied. In a final, fifth, set of experiments, thirty-three surgically excised or biopsied melanocyte lesions, including fourteen malignant melanomas (comprising thirteen from skin with Breslow depth from 0.275 mm to 1.3 cm and one from metastasis in soft tissue of the arm), eight dysplastic nevi, and eleven benign nevi (all of which may, collectively, be referred to as pigmented skin lesions) were immunohistochemically studied.

Procedures

The tissue biopsies were sectioned by microtome at 4 um and mounted on charged slides. The tissue samples on slides were deparaffinized according to established procedures and, and, in some cases, rehydrated in graded alcohols. Generally, the samples were then washed in running water and Tris buffer saline (TBS) consisting of 50 mM Tris-HCl (pH 7.6), 150 mM NaCl and 0.05% Tween 20. Next, the slides were pretreated with heat-induced epitope retrieval in Target Retrieval Solution pH 9.0 or pH 6.0 (provided by Dako, Glostrup Denmark), and cooled for between fifteen and twenty minutes at room temperature.

Immunohistochemistry was performed using the EnVision+ System, HRP (Dako) and performed either manually (with or without humid chamber) or using the Dako Autostainer. Endogenous peroxidase was quenched by incubating sections in 3% hydrogen peroxide for five to six minutes. Mouse monoclonal anti-human L523S (Dako) clone 69.1 was used at a concentration of 0.5 µg/ml on tissue pretreated with a 30-40 minute heating protocol. Mouse monoclonal anti-human desmin (Dako) clone D33 was used at 4.7 µg/ml on tissue pretreated with a 20-minute heating protocol. Lung pleural tissue biopsies and pleural effusions were also stained with calretinin. For these, mouse monoclonal anti-human calretinin (Dako) clone DAK Calret 1 was used at 1.3 µg/ml on tissue pretreated with a 20-minute heating protocol. Lung pleural effusion samples were also stained with CK 5/6. In many cases, a negative control reagent was also used with each tissue sample to confirm the specificity of the immunostaining. The various primary antibodies were applied to the tissue and incubated for between thirty and sixty minutes, depending upon sample, and slides were rinsed with Tris-Buffered Saline with Tween (TBST). Bound antibody was detected by incubating with a peroxidase-conjugated Envision+ polymer detection system, which, in addition, also carries secondary link antibody molecules (rabbit or mouse) (Dako), or goat-anti-rabbit or horse-anti-mouse IgG-biotin and streptavidin-HRP for 30 minutes. Finally, the slides were incubated in 3,3'-diaminobenzidine (DAB+) substrate/chromogen solution or AEC+Substrate-Chromogen (Dako), depending upon sample, for 10 minutes, rinsed in DI water, counterstained with hematoxylin and mounted and viewed under a light microscope.

Figure 1A:
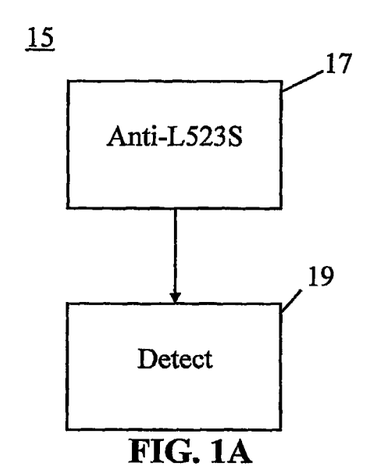
FIG. 1A is a flow chart that schematically illustrates a first method for distinguishing malignant tissue or cells in accordance with the invention.
Figure 1B:
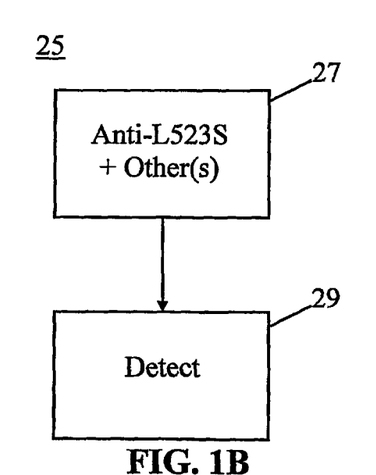
FIG. 1B is a flow chart that schematically illustrates a second method for distinguishing malignant tissue or cells in accordance with the invention.

Accordingly, modes for carrying out the invention are summarized in and may be understood with reference to FIG. 1A and FIG. 1B, which are flow charts that schematically illustrate first and second methods for differentiating between normal or reactive cells and malignant cells in a biological sample in accordance with the present invention. The first method 15, schematically illustrated in FIG. 1A, comprises two steps. In the first step 17, the biological sample, or a portion of the biological sample, is exposed to an antibody to L523S protein, so as to enable the antibody to bind to this marker protein (if any). Subsequently, in the second step 19, the antibody that has bound to L235S within the sample is then detected. A detected level or amount above or greater some pre-determined threshold is then taken as a positive indication of malignancy or of the aggressiveness or grade of the malignancy. As one example, both the intensity of cytoplasmic staining (0 to 3+) and the percentage of cells stained (0-100%) may be recorded in step 19, with positive staining being defined as 2+ or 3+ intensity (for example) in 10% or more cells (for example). As another example, positive staining may be defined as instances in which more than 10% of cells show cytoplasmic staining of any staining intensity.

In general, the detection of the bound antibody will be achieved by detecting some label, such as a chromogen or fluorochrome. In general, this detection will be through microscopic analysis, either manual or automated. The biological sample will often be a tissue biopsy but may, instead, be a biological fluid, such as a sample of lung pleural effusion. Often, only a portion of a biological sample, rather than the entire biological sample, will be exposed to an antibody to L523S protein in step 17. If the sample is a tissue sample, the portion may, for instance, be a thin slice of the tissue sample as produced by a microtome. If the sample is of a body fluid or derived or taken from a body fluid, then the sample portion may assume one of a variety of different physical configurations, such as a cell monolayer formed by swabbing or smearing the fluid onto a microscope slide (e.g., a smear) or by centrifugation of the fluid or a cell pellet formed by centrifugation of the fluid. Although the intensity and location of staining of stained biological samples are frequently determined visually by microscopy of samples mounted on slides, flow cytometry techniques could instead be used to detect and enumerate cells (disaggregated and derived from either from either tissue or fluid samples) having one or more types of chemical labels specific to the markers described herein.

The second method 25, schematically illustrated in FIG. 1B, represents a modification of the first method 15. In the first step 27 of method 25, a biological sample is exposed to an antibody to L523S protein and is also exposed to an antibody to at least one other marker protein, so as to enable the antibody to L523S to bind to L523S in the sample (if any) and so as to enable the second antibody to bind to the at least one other marker protein. The second marker protein may, for instance, be a marker to cell lineage, such as calretinin, which is a marker of mesothelial cell lineage. Alternatively, the second marker protein may be a marker of cells that are normal or reactive, such as desmin. More than one such "second" marker may be employed in a single set of tests or on a single sample. Subsequently, in the second step 29, the bound antibodies (if any) are detected as described previously. These multiple markers may be detected in an individual section or specimen (e.g., a tissue section or a cell monolayer or pellet derived or prepared from a body fluid) through multi-staining of the section or specimen. Alternatively, in this method, it may be advantageous to expose different portions of the sample, such as serial sections from a sample biopsy, to the different respective antibodies. If the sample is of a body fluid or taken from a body fluid, then the different portions may comprise different sections of one or more cell pellets or may comprise different cell monolayer preparations formed by centrifugation or smearing.

Results

Results from Studies of Luna Pleural Tissue Biopsies.

In order to appreciate the practice and advantages of the present invention, the reader is referred to the accompanying FIGS. 2-5 in conjunction with the following discussion, which illustrate and describe immunohistochemical staining results biopsies of lung pleural tissue. It is to be noted that the accompanying FIGS. 2-5 are only intended to be exemplary of the results obtained by employing methods in accordance with the present invention and are not intended to be in any way limiting of the invention. In the accompanying figures, staining with the DAB+ substrate-chromogen solution results in a brown-colored precipitate (appearing as dark gray to black in the accompanying drawings) at the antigen sites whereas the counterstaining with hematoxylin results in the blue-purple precipitate haematein (appearing as light to medium gray in the accompanying drawings) at cell nuclei. Cells staining positive for Calretinin and desmin also appear as dark gray to black in the accompanying drawings.

Although the present invention is described in terms of immunohistochemical staining methods that produce readily visualized colored precipitates within biological samples, it is to be understood that the invention is considered to encompass a variety of known immunohistochemical techniques for visualization of antigen sites. For instance, the so-called "direct" method of immunohistochemical staining could be used, in which a single labeled antibody that binds directly to the target antigen is detected, either optically or otherwise. Alternatively, any "indirect method" of staining may be employed, wherein an unlabeled primary antibody reacts with tissue antigen, and a labeled secondary antibody that reacts with the primary antibody is detected. Still further, the staining method may include utilizing, instead of the simple secondary antibody, a reagent of the type described in U.S. Pat. No. 5,543,332, incorporated herein by reference, in which secondary antibody molecules are carried on an enzyme-conjugated polymer backbone. The enzyme, when allowed to catalyze a substrate so as to form a colored reaction product, acts as a label of the reagent which can be detected via the colored reaction product Such reagents are marketed under the trade name EnVision by Dako of Glostrup Denmark. In either case, the label could comprise, for instance, either individually or in combination, a chromogen, a fluorescent dye such as FITC, rhodamine or Texas red, an enzyme such as peroxidase, alkaline phosphatase or glucose oxidase, a chemiluminescent, material, or a molecule containing a radioactive isotope, magnetic particles, etc.

Figure 2A:
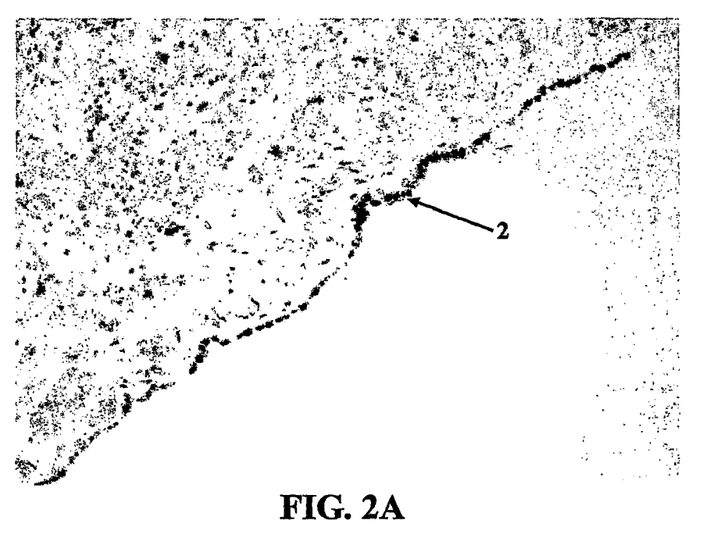
FIG. 2A shows a photomicrograph of normal lung pleura immunostained with anti-Calretinin demonstrating normal mesothelial cells positively stained in a line on the edge of the tissue.
Figure 2B:
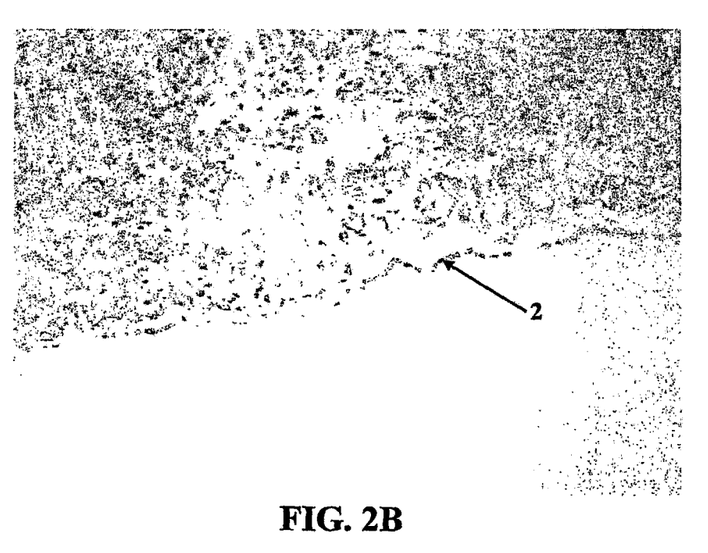
FIG. 2B shows a photomicrograph of a serial section of the normal lung pleura of FIG. 1A immunostained with anti-L523S demonstrating a lack of immunoreactivity of anti-L523S with normal mesothelial cells present.
Figure 3A:
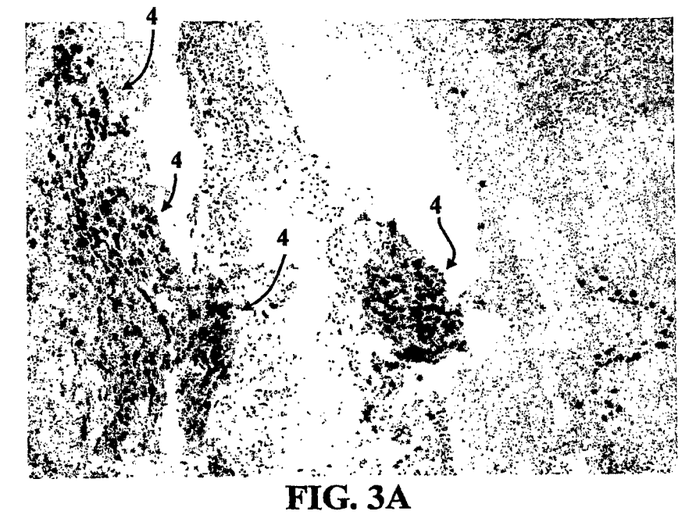
FIG. 3A shows a photomicrograph of reactive mesothelial cells within a normal lung pleural biopsy immunostained with anti-Calretinin, demonstrating positively stained reactive mesothelial cells.
Figure 3B:
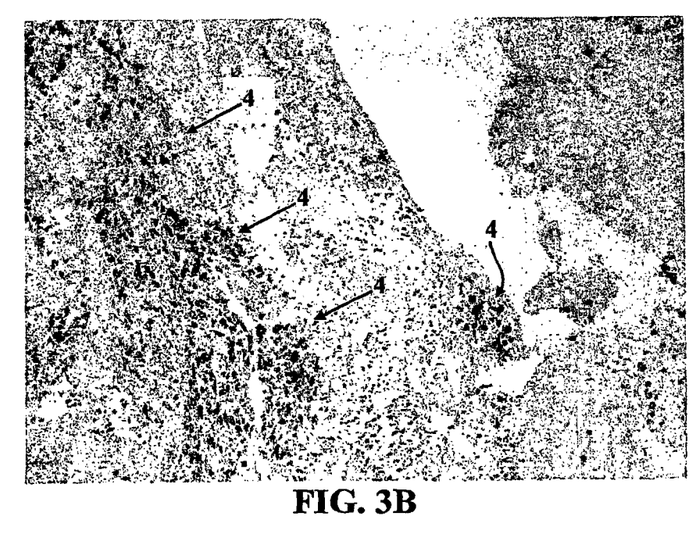
FIG. 3B shows a photomicrograph of a serial section of the lung pleural biopsy of FIG. 3A immunostained with anti-desmin demonstrating positively stained reactive mesothelial cells.
Figure 3C:
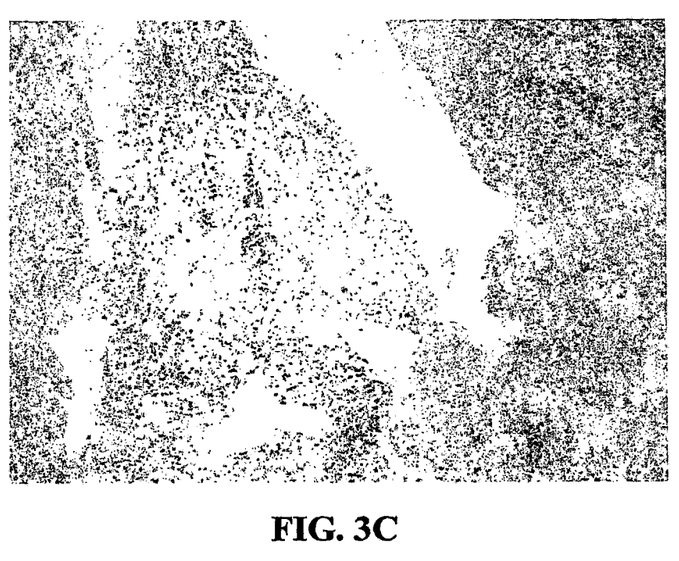
FIG. 3C shows a photomicrograph of a serial section of the lung pleural biopsy of FIG. 3A immunostained with anti-L523S demonstrating a lack of immunostaining of anti-L523S with reactive mesothelial cells.

Returning, once again, to the discussion of the figures, normal mesothelial cells 2 were identified in human lung pleural biopsies using immunohistochemistry by their positivity for Calretinin (FIG. 2A, dark-colored zone) and lack of L523S expression (FIG. 2B). Reactive mesothelial cells 4 positively immunostained for Calretinin (FIG. 3A, dark colored region) and desmin (FIG. 3B), but were also negative for L523S (FIG. 3C). In all, nine normal lung pleural biopsies, anti-L523S was unreactive with normal and reactive mesothelial cells, while anti-desmin positively immunostained both normal and reactive mesothelial cells in eight of the nine normal lung pleural biopsies. Desmin expression was found to be more intense in reactive mesothelial cells compared to normal mesothelial cells. Normal human pericardial mesothelial cells were found to be immunoreactive with anti-L523S, demonstrating that specific types of mesothelial cells can express L523S protein (data not shown).

Figure 4A:
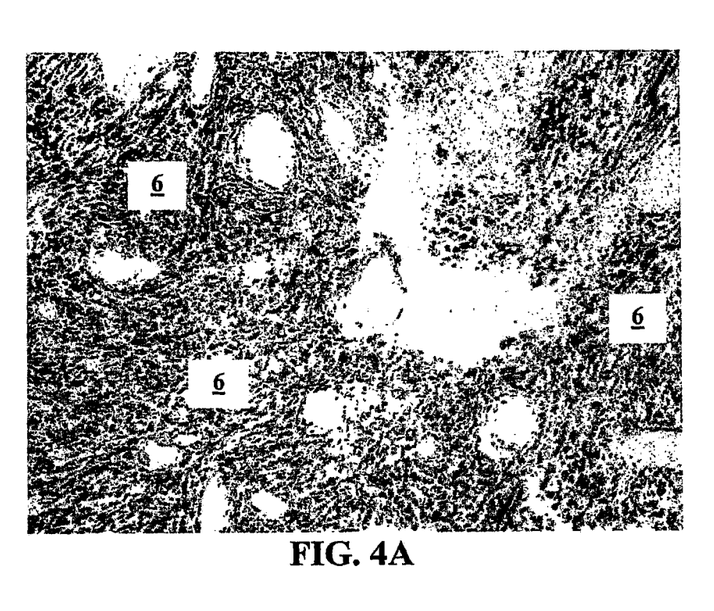
FIG. 4A is a photomicrograph of a lung pleural biopsy with mesothelioma immunostained with anti-L523S.
Figure 4B:
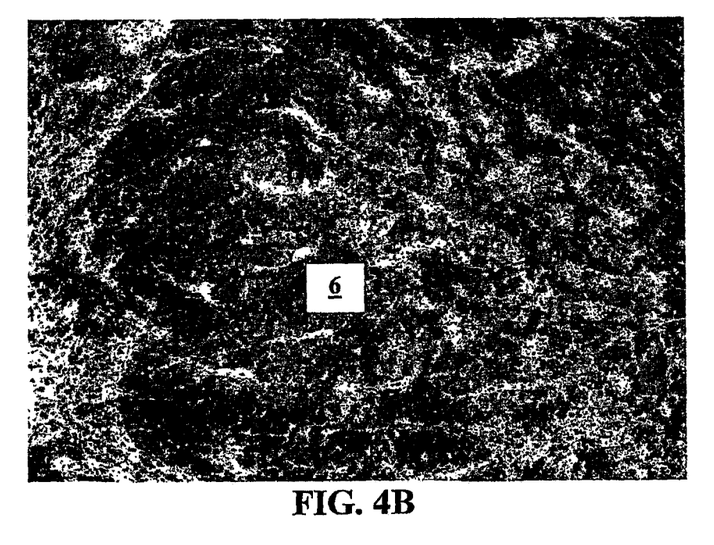
FIG. 4B is a photomicrograph of a lung pleural biopsy with melanoma immunostained with anti-L523S.
Figure 4C:
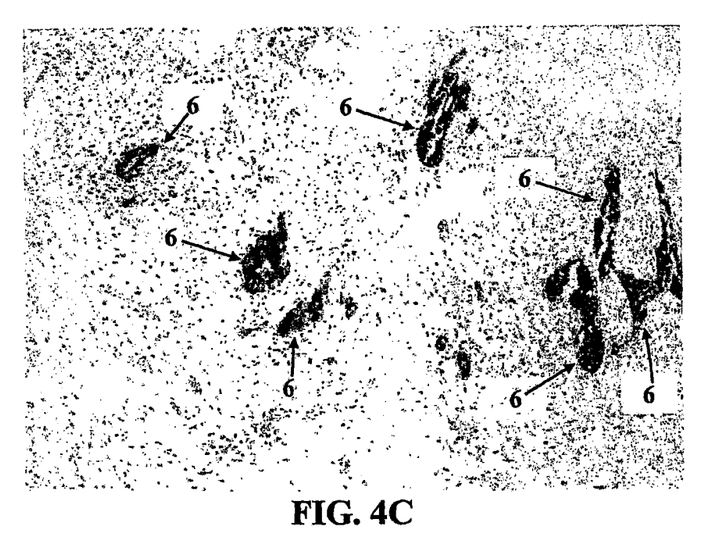
FIG. 4C is a photomicrograph of a lung pleural biopsy with lung adenocarcinoma immunostained with anti-L523S.
Figure 4D:
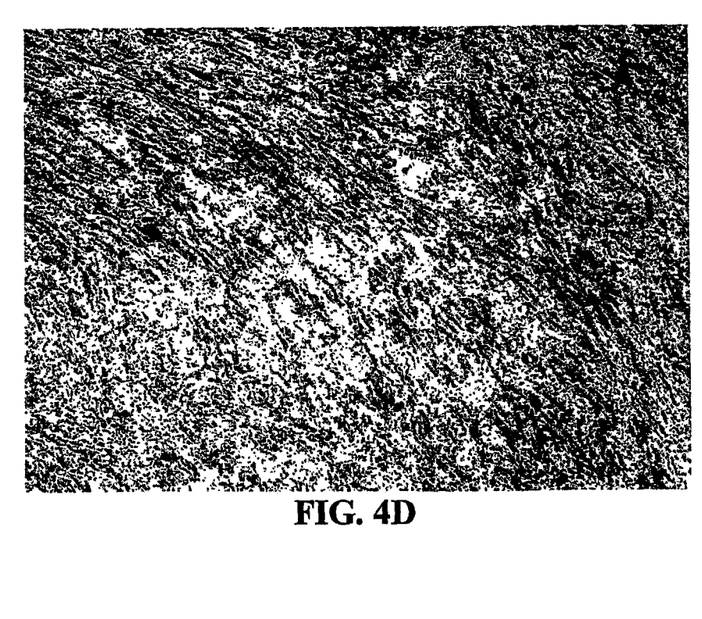
FIG. 4D is a photomicrograph of a lung pleural biopsy with lung spindle cell carcinoma immunostained with anti-L523S.
Figure 4E:
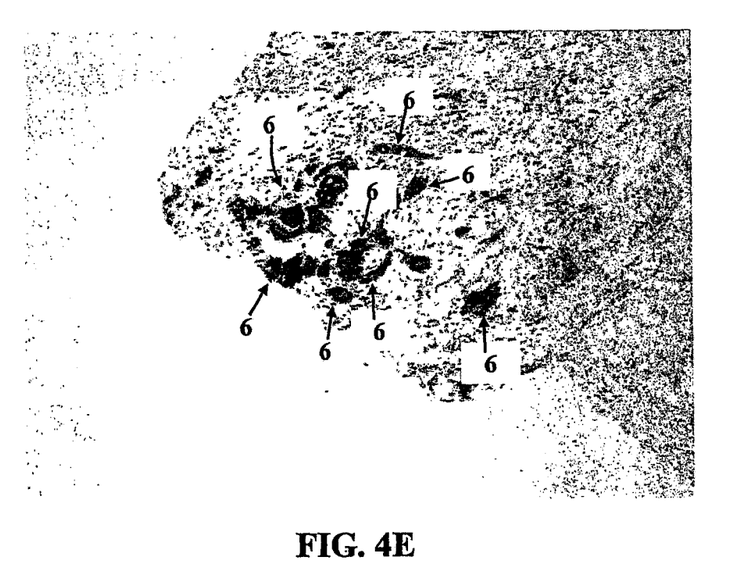
FIG. 4E is a photomicrograph of a lung pleural biopsy with lung squamous cell carcinoma immunostained with anti-L523S.
Figure 5A:
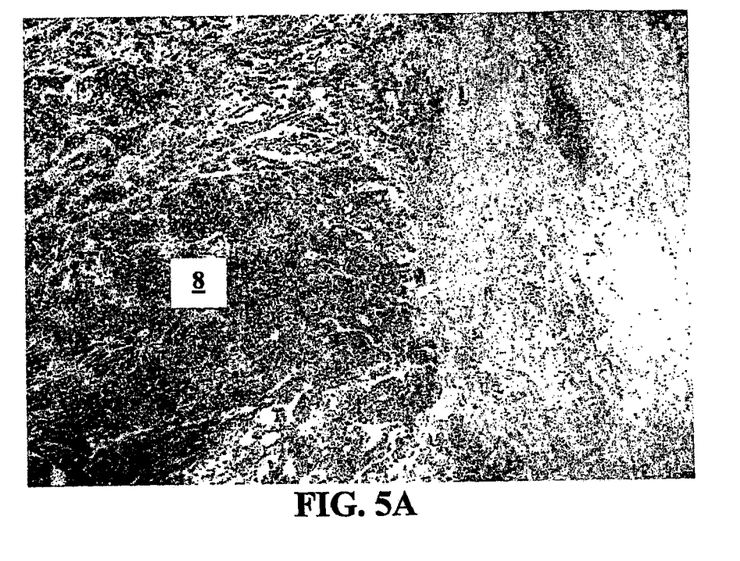
FIG. 5A is a photomicrograph of a lung pleural biopsy containing mesothelioma immunostained with anti-L523S, demonstrating cytoplasmic staining within the cancer cells.
Figure 5B:
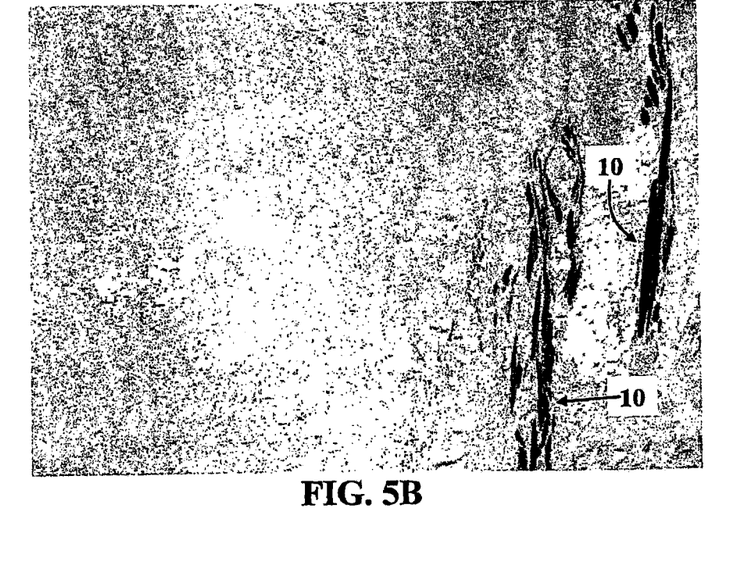
FIG. 5B is a photomicrograph of a serial section of the lung pleural biopsy of FIG. 4A immunostained with anti-desmin showing positive staining of only muscle elements of the tissue.

Using the novel immunohistochemistry staining method described above, L523S protein expression—that is, cells 6 staining positive for L523S—was identified in malignant cells in eight of thirteen (including two weak positives) lung pleural biopsies containing mesothelioma (FIG. 4A); in one (of one) lung pleural biopsy containing melanoma (FIG. 4B); in three of three lung pleural biopsies containing adenocarcinoma (FIG. 4C); in one (of one) lung pleural biopsy containing spindle cell carcinoma (FIG. 4D) and in one (of one) lung pleural biopsy containing squamous cell carcinoma (FIG. 4E). Anti-L523S also demonstrated some immunoreactivity in non-cancer cells and in secretions such as: lung secretions (rare), subset of normal bronchi (faint staining), germinal center of the lymph node and reactive fibroblasts or activated lymphocytes (rare). In contrast, anti-desmin was unreactive with malignant cells, though many normal muscle cells were positively immunostained in the biopsies (FIG. 5B). Interestingly, cells not identified as muscle did positively immunostain with anti-desmin in two cases of mesothelioma. These small groups of cells are likely reactive mesothelial cells. FIGS. 5A-5B demonstrate the contrasting staining pattern seen with anti-L523S compared to anti-desmin on a lung pleural biopsy containing mesothelioma, where L523S immunoreactivity can be seen within the cytoplasm of the cancer cells (seen in FIG. 5A as cytoplasm of tumor cells 8 that are positively stained for L523S expression), and desmin expression is present only in the muscle elements 10 of the tissue (FIG. 5B).

Results from Studies of Biopsies of Lung Neuroendocrine Tumors.

In our immunohistochemical analyses, nine SCLCs (90%) showed a strong and diffuse (more than 90% of tumor cells) cytoplasmic staining pattern for L523S, and only 1 case exhibited focal immunoreactivity. Nine of fourteen LCNECs (64%) showed strong cytoplasmic staining detected in greater than 90% of the tumor cells. The remaining 5 cases exhibited a variable degree of immunoreactivity, but none of the cases were completely negative for L523S expression. No positive staining for L523S was detected in any of the sixteen typical carcinoids. Five of six atypical carcinoids also showed a complete lack of immunoreactivity, with only a single atypical carcinoid exhibiting weak staining in areas exhibiting oncocytic changes.

Results from Pleural Effusion Samples.

In thirty-five malignant pleural effusion samples positive staining for L523S in a variable degree of intensity was observed in 28 (80%) cases, including 100% of mesotheliomas, 100% of lung adenocarcinomas, 100% of small cell and squamous cell carcinomas, 75% of colonic adenocarcinomas and 14% of breast adenocarcinomas. Sixteen cases diagnosed as reactive mesothelial cells showed positivity for calretinin and thirteen of sixteen were CK5/6 positive. Interestingly, mesothelial cells were positive for L523S in two of sixteen cases originally interpreted as benign. One of these was diagnosed as malignant mesothelioma on pleural biopsy. All malignant mesotheliomas were positive for calretinin, and eight of ten cases had CK5/6 staining.

Results from Studies of Biopsies of Bladder Urothelial Tissue.

Positive staining was observed in the majority of lesions in the high grade group, including invasive urothelial carcinoma, urothelial carcinoma in-situ, and high grade papillary urothelial carcinoma. No expression of L523S was detected in low grade papillary urothelial carcinoma, and the group of benign to borderline lesions, including normal urothelium (fourteen samples), papillary urothelial neoplasm of low malignant potential (three samples) and urothelial atypia of unknown significance (a single sample). Expression of L523S between low grade papillary urothelial carcinoma and each lesion in the high grade group was statistically significant, as was that between benign to borderline group and each lesion of the high grade group.

Results from Biopsies of Pigmented Skin Lesions.

Seven of fourteen (50%) malignant melanomas, including one metastatic melanoma in soft tissue of the arm, showed moderate to strong positive staining for L523S, with four cases exhibiting positivity in >90% of tumor cells and three cases showing positivity in 10-20% of tumor cells. All four (100%) cases with Breslow depth of >1.3 mm showed moderate to strong positive staining for L523S while two of nine (22%) cases with Breslow depth 1.3 mm exhibited moderate to strong positive staining for L523S, and they are significantly different (p<0.05). No positive L523S staining was detected in 8 dysplastic nevi and 11 benign nevi.

CONCLUSIONS

In total, tissues from all of the following tumors have been tested according to the methods of the present invention and found to be immunoreactive with anti-L523S: mesothelioma, melanoma, lung adenocarcinoma, squamous cell carcinoma, spindle cell carcinoma, colonic adenocarcinoma, ovarian carcinoma, gastric carcinoma, pancreatic carcinoma, astrocytoma, Hodgkin's lymphoma, lymphoma, malignant fibrous histocytoma, Ewing's Sarcoma and carcinoids. As but one example, differentiating reactive mesothelial cells from malignant cells in human lung pleural biopsies by traditional methods can be challenging. However, the novel immunohistochemistry staining method disclosed herein provides a new tool to aid in this differential. Anti-L523S may have utility as a marker of malignancy in this diagnostic setting because it does not react with normal and reactive lung pleural mesothelial cells, but is expressed in many cancers. In this study, L523S expression was demonstrated in 8/13 mesotheliomas, 1/1 melanoma, 3/3 adenocarcinomas, 1/1 spindle cell carcinoma and 1/1 squamous cell carcinoma found in lung pleural biopsies. While L523S was not expressed in all of the cancerous cells tested, a positive result can assist in differentiating malignant cells from benign mesothelial cells.

The use of additional antibodies such as anti-desmin and anti-calretinin may further aid in differentiating between reactive mesothelial cells and malignant cells. Anti-desmin can confirm the presence of normal or reactive mesothelial cells on the specimen, while anti-calretinin as a mesothelial cell marker can indicate that benign or malignant cells are of mesothelial origin. Further, the use of a panel of markers in immunohistochemistry, which includes anti-L523S and anti-desmin can aid in differentiating between reactive lung pleural mesothelial cells and malignant cells.

We also conclude that L523S is highly expressed in high grade lung neuroendocrine carcinomas, but not in low and intermediate grade carcinoid tumors, indicating that L523S may be used as a diagnostic immunomarker in the distinction between high grade and low/intermediate grade lung neuroendocrine tumors, particularly when the diagnostic material is limited with crush artifact. We further conclude that L523S is a sensitive and specific marker for detection of malignant cells in pleural effusion, and that it has significant utility in diagnosis of reactive mesothelial cells, malignant mesothelioma and metastatic carcinoma in combination with calretinin and CK5/6 staining.

We further conclude that L523S is overexpressed in high grade papillary urothelial carcinoma and urothelial carcinoma in-situ, in comparison to benign urothelium and borderline and low grade lesions and, consequently, immunohistochemical staining for this marker may help in grading difficult cases of urothelial tumors. We still further conclude that L523S is expressed in malignant melanoma but not in melanocyte nevi even when dysplastic features are present, that positive detection of this marker parallels Breslow depth of invasion and that L523S is a marker of aggressiveness in the malignant melanoma.

A novel method for immunoreaction and staining of anti-L523s on normal and malignant biological samples has been disclosed. As can be easily understood from the foregoing, the basic concepts of the present invention may be embodied in a variety of ways. The essence of the invention includes not only sample processing techniques but, also, the various systems, assemblies, and devices required or usable to accomplish the sample processing. Various modifications and variations of the described methods and system of the invention will be apparent to those skilled in the art without departing from the scope and spirit of the invention. Although the invention has been described in connection with specific preferred embodiments, it should be understood that the invention as claimed is not intended to be and should not be unduly limited to such specific embodiments. Indeed, various modifications of the described modes for carrying out the invention which are obvious to those skilled in diagnostic pathology or related fields are intended to be within the scope of the claims. Note that any patents, patent applications, publications, or other references mentioned in this application for patent are hereby incorporated herein by reference.

The invention claimed is:

1. A method of detecting L523S protein in a biological sample comprising normal or reactive and malignant cells, said method comprising:
   (a) obtaining a biological sample;
   (b) contacting the biological sample with an anti-L523S antibody, and detecting the binding between L523S protein and the antibody;
   (c) contacting the biological sample with an antibody to a second protein that is a marker of cell lineage, and detecting the binding of the antibody to the second protein; and
   (d) contacting the biological sample with an antibody to a third protein whose expression is restricted to normal or reactive cells, and detecting the binding of the antibody to the third protein;
   thereby producing cells having L523S protein bound to the anti-L523S antibody, the second protein bound to the antibody to the second protein, and the third protein bound to the antibody to the third protein;
   wherein the normal or reactive cells and malignant cells are mesothelial cells.

2. The method of claim 1, wherein the second protein is calretinin.

3. The method of claim 1, wherein the third protein is desmin.

4. The method of claim 1, wherein at least one detecting step comprises detecting an immunohistochemical stain or flow cytometric evaluation.

5. The method of claim 1, wherein the biological sample is a tissue biopsy, biological fluid, cell monolayer, or cell pellet derived from a biological fluid.

6. The method according to claim 5, wherein the biological fluid is lung pleural effusion.

7. The method of claim 1, wherein step (b) further comprises:
   exposing the biological sample to a labeled secondary antibody that reacts with the antibody bound to L523S protein; and
   detecting the presence of the secondary antibody bound to the antibody bound to L523S protein.

8. The method of claim 1, wherein step (b) further comprises:
   exposing the biological sample to a labeled reagent comprising an enzyme-conjugated polymer backbone that carries secondary antibody molecules that react with the antibody bound to L523S protein; and
   detecting the presence of the labeled reagent.

9. The method of claim 5, wherein the biological sample is a tissue biopsy, and wherein step (a) is performed on a first portion of the tissue biopsy, step (b) is performed on a second portion of the tissue biopsy, and step (c) is performed on a third portion of the tissue biopsy.

10. The method of claim 9, wherein the first and second portions are different microtomed sections from the same tissue biopsy.

11. The method of claim 9, wherein the first, second and third portions are different microtomed sections from the same tissue biopsy.

12. The method of claim 1, wherein step (c) further comprises:
   exposing the biological sample to a labeled secondary antibody that reacts with the antibody bound to the second protein; and
   detecting the presence of the secondary antibody bound to the antibody bound to the second protein.

13. The method of claim 1, wherein step (c) further comprises:
   exposing the biological sample to a labeled reagent comprising an enzyme-conjugated polymer backbone that carries secondary antibody molecules that react with the antibody bound to the second protein; and
   detecting the presence of the labeled reagent.

14. The method of claim 1, wherein step (d) further comprises:
   exposing the biological sample to a labeled secondary antibody that reacts with the antibody bound to the third protein; and
   detecting the presence of the secondary antibody bound to the antibody bound to the third protein.

15. The method of claim 1, wherein step (d) further comprises:
   exposing the biological sample to a labeled reagent comprising an enzyme-conjugated polymer backbone that carries secondary antibody molecules that react with the antibody bound to the third protein; and
   detecting the presence of the labeled reagent.

* * * * *